United States Patent
Dong (10) Patent No.: US 7,933,439 B2
(45) Date of Patent: Apr. 26, 2011

(54) ULTRASOUND IMAGING METHOD AND APPARTUS FOR ADAPTIVELY SUPPRESSING TISSUE FLICKERING

(75) Inventor: Yongqiang Dong, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 390 days.

(21) Appl. No.: 12/334,235

(22) Filed: Dec. 12, 2008

(65) Prior Publication Data

US 2009/0227868 A1    Sep. 10, 2009

(30) Foreign Application Priority Data

Mar. 4, 2008   (CN) .......................... 2008 1 0065766

(51) Int. Cl.
*G06K 9/00*      (2006.01)
*A61B 8/00*      (2006.01)
(52) U.S. Cl. .................... 382/130; 382/168; 600/443
(58) Field of Classification Search .............. 382/100, 382/128, 129, 130, 131, 132, 133, 134, 162, 382/165, 168, 172, 173, 181, 199, 274, 275, 382/286, 305, 312; 600/443, 454; 73/602; 378/5, 18, 29
See application file for complete search history.

(56) References Cited

U.S. PATENT DOCUMENTS

| | | | | |
|---|---|---|---|---|
| 4,751,846 A * | 6/1988 | Dousse | ........................... | 73/602 |
| 6,238,345 B1 * | 5/2001 | Wissler et al. | ................ | 600/443 |
| 6,423,003 B1 * | 7/2002 | Ustuner et al. | ................ | 600/443 |
| 6,458,083 B1 * | 10/2002 | Jago et al. | ...................... | 600/443 |
| 6,641,536 B2 * | 11/2003 | Hossack et al. | ............... | 600/443 |
| 7,044,913 B2 * | 5/2006 | Shiki | ............................. | 600/454 |

FOREIGN PATENT DOCUMENTS

CN   1516916 A   7/2004
CN   1919144 A   2/2007

* cited by examiner

*Primary Examiner* — Seyed Azarian
(74) *Attorney, Agent, or Firm* — Kory D. Christensen; Stoel Rives LLP (57) ABSTRACT

The present disclosure provides an ultrasound imaging method and apparatus for adaptively suppressing tissue flickering. The method includes transmitting ultrasound pulses to an object to be detected and receiving ultrasound echo signals from the object to be detected; processing the ultrasound echo signals to obtain anatomical image data; demodulating the ultrasound echo signals to obtain demodulated signals; processing the demodulated signals to obtain blood flow image data; and displaying either anatomical image data or blood flow image data based on fusing rules, wherein a first fusing rule is used for a portion of the object to be detected in which tissue flickering exists, and a second fusing rule, which is different from the first fusing rule, is used for a portion of the object to be detected in which no tissue flickering exists.

17 Claims, 6 Drawing Sheets

ULTRASOUND IMAGING METHOD AND APPARTUS FOR ADAPTIVELY SUPPRESSING TISSUE FLICKERING

CROSS-REFERENCE TO RELATED APPLICATIONS

This application claims priority to Chinese Patent Application No. 200810065766.2, filed Mar. 4, 2008, for "ULTRASOUND IMAGING METHOD AND APPARATUS FOR ADAPTIVELY SUPPRESSING TISSUE FLICKERING," which is incorporated herein by reference.

TECHNICAL FIELD

The present disclosure relates to the field of ultrasound imaging, and more particularly, to an ultrasound imaging method and apparatus for adaptively suppressing tissue-flickering.

SUMMARY

A method and apparatus for reducing or eliminating tissue flickering caused by various tissue motions in an ultrasound imaging system is disclosed.

DETAILED DESCRIPTION

A color ultrasound imaging system uses the Doppler effect to detect the motion parameters of flowing blood and visceral organs in a human body. A Doppler frequency shift of human body tissue relative to a probe will be caused due to heartbeat, respiration, periodic contraction and expansion of blood vessel walls, or the motion of the probe relative to a human body.

This tissue motion is rather complicated. It may be either a simplex motion of a tissue relative to the probe, a reciprocating motion of a tissue relative to the probe, or even a twist. With respect to a simplex motion of a tissue, when the Doppler frequency shift of tissue motion is larger than that of a slow blood flow to be detected, clutter residues outputted from a wall filter will be larger. For a complex reciprocating tissue motion and a twist, the frequency spectrum will not be a simple translation of the frequency spectrum of a stationary object along the Doppler frequency axis. The entire frequency spectrum will instead be raised. Although the mean Doppler frequency shift is not necessarily large, clutter residues outputted from various adaptive wall filters are still large. When the Doppler frequency shift of the tissue motion is larger than that of the blood flow to be detected, or when the energy of wall-filtered clutter residues is larger than that of the blood flow to be detected, it is possible that this tissue motion will appear in the final image displayed. The appearance of motion parameters of this tissue motion in a color blood flow pattern image is referred to as "tissue flickering."

The problem of tissue flickering has increased in importance with the emergence of color ultrasound imaging. One approach to eliminating tissue flickering is frequency spectrum shifting. The method detects blood flow signals by (1) estimating the Doppler frequency shift of a tissue motion, (2) generating frequency spectrum shifting signals for demodulated signals based on the estimated Doppler frequency shift, and (3) frequency shifting the demodulated signals, thereby shifting the Doppler frequency shift of the tissue motion to a direct current, and then suppressing tissue echoes through a wall filter.

According to another approach, a wall filter uses a complex coefficient, thereby forming a wall filter with bilaterally asymmetric magnitude versus frequency response, with the notch of the wall filter just aligned with the shifted tissue motion frequency spectrum. The location of the filter notch can be set based on the frequency of the tissue motion, and the cutoff frequency of the filter can be set based on the bandwidth (variance) of the tissue motion.

In yet another approach, the wall filter is a filter with bilaterally symmetric magnitude versus frequency response, while the cutoff frequency of the filter can be adjusted based on the frequency and variance of the tissue motion to achieve approximately the effect of a complex coefficient filter.

In a dual-channel adaptive wall filter approach, a signal passes through two wall filters with different cutoff frequencies, and then the velocity, energy, and variance of "blood flow" are estimated respectively via auto-correlation. Based on different mapping results of tissues and blood flows by the wall filters with different cutoff frequencies, a differentiation between tissue flickering and the blood flow may be made in parameter space (energy, velocity, variance), thereby suppressing tissue flickering.

Still another approach involves an adaptive regression filter for separating tissue echoes from blood flow echoes. A differentiation between the tissue and the blood flow is made by calculating the characteristic value of auto-correlation matrix of echoes.

The aforementioned adaptive wall filtering techniques may be divided into 4 categories: frequency spectrum shifting, adjustment of cutoff frequency, dual-channel, and characteristic vector decomposition of the correlation matrix.

Since the tissue motion in a human body is rather complicated, in a correlation processing, the tissue motion is not necessarily a simplex unidirectional motion, but may be a motion towards a probe for a period of time, away from the probe for another period of time and then again towards the probe, or may be a twist. For the probe, a twist case in which no tissue motion occurs for some sampling moments while the tissue motion occurs for some sampling moments at a sampling point within the correlation processing period. In case of estimating tissue motion parameters by using tissue echoes, when a stationary tissue component exists, the estimated frequency of the tissue motion will be on the low side; when the stationary tissue component is larger than the motion component, the estimated velocity will be on the low side. Therefore, according to frequency spectrum shifting, it is not required to shift the echo frequency spectrum at such times, or there is insufficient shifting of the echo frequency spectrum. Therefore, after wall-filtering, there are still very strong tissue residues, resulting in the appearance of the tissue motion in the final image.

Adjustment of the cutoff frequency relates to adjusting the cutoff frequency of a wall filter based on the estimated tissue motion velocity or the combination of the estimated tissue motion velocity and tissue motion variance. This method suffers from the same problem as the frequency spectrum shifting. When the estimated tissue motion velocity cannot correctly reflect a real tissue motion, the wall filter cutoff frequency set only based on the tissue motion frequency will be on the low side, again causing the tissue energy remaining after wall-filtering to be on the high side and tissue flickering to be displayed in the image. Although the setting of the wall filter cutoff frequency may be corrected by using the variance, since the number of points of correlation processing in the color mode is too small, the difference between the tissue motion variances of the stationary tissue and the twisting tissue is very small, the wall filter cutoff frequency can not be corrected to an ideal position.

Treating a wall filter as a kind of signal transformation, the dual-channel method transforms the demodulated signals into different positions in the parameter space (energy, velocity, and variance) through wall filters with different cutoff frequencies, and then differentiates between tissue flickering and the blood flow based on the distribution of two groups of different parameters. The energy of the tissue residue with a low cutoff frequency is high, while the energy of the tissue residue with a high cutoff frequency is little or none, by which some tissue flickering can be removed. Furthermore, the velocity of a channel with a low cutoff frequency is not high when the energy is strong, and the energy becomes smaller and the velocity becomes higher at the same place when the cutoff frequency is high, but the magnitude of the velocity increase is not large. In this way, some tissue flickering may also be determined. A disadvantage with the dual-channel method is that tissue flickering is determined by using the distribution of two groups of different parameters (energy, velocity, variance), but the parameter distribution among different persons or different detected parts are hugely different, causing this method to be too sensitive to parameters.

With regard to the method for characteristic decomposition of correlation matrix, it is generally required to first calculate the auto-correlation matrix of echoes in real time and perform the characteristic decomposition of the correlation matrix in real time. Therefore, the computational complexity is very high. Additionally, it is sometimes difficult in practice to differentiate between tissue flickering and the blood flow by using the characteristic values. When the energy of the twisting tissue at a higher Doppler frequency is smaller than that of the blood flow at a lower Doppler frequency, i.e., when the characteristic value of the tissue at a high Doppler frequency is smaller than that of the blood flow at a low Doppler frequency, the blood flow is often suppressed while tissue flickering remains.

The present disclosure provides an ultrasound imaging method for adaptively suppressing tissue flickering. The method may include a transmitting and receiving step for transmitting ultrasound pulses to an object to be detected, and for receiving ultrasound echo signals from the object to be detected. The method may also include an envelope detecting step for processing the ultrasound echo signals to obtain anatomical image data, as well as a signal processing step for processing the ultrasound echo signals to obtain demodulated signals. In one embodiment, the method includes a blood flow processing step for processing the demodulated signals to obtain blood flow image data. The method may include a displaying step for displaying either the anatomical image data or the blood flow image data based on fusing rules, wherein the displaying step comprises using a first fusing rule for a portion of the object to be detected in which tissue flickering exists, and using a second fusing rule, which differs from the first fusing rule, for a portion of the object to be detected in which no tissue flickering exists.

In one embodiment, the method further comprises a tissue flickering determination step for determining the portion of the object to be detected in which tissue flickering exists and the portion in which no tissue flickering exists. The tissue-flickering determination may include a filtering step for filtering out stationary tissue components from the demodulated signals to obtain motion components, a parameter estimation step for estimating tissue motion parameters based on the motion components, and a tissue-flickering decision step for deciding the existence of tissue flickering in the object to be detected based on the tissue motion parameters and for providing a tissue-flickering flag.

The filtering step may include zero-order linear polynomial regression filtering, infinite impulse response filtering, or finite impulse response filtering.

In one embodiment, the parameter estimation step includes performing auto-correlation estimation on the motion components to obtain the tissue motion parameters.

In one embodiment, the tissue-flickering decision step includes comparing the tissue motion parameters with corresponding parameter threshold values.

In one embodiment, the tissue-flickering decision step includes deciding the existence of tissue flickering in the object to be detected based on a lookup table.

In one embodiment, the tissue-flickering decision step includes using a frame of two-value image to represent the tissue-flickering flag distribution in the object to be detected, wherein each tissue-flickering flag is denoted by one bit.

In one embodiment, the tissue-flickering determination step further includes a tissue-flickering flag reconfirmation step for reconfirming tissue-flickering flags in the two-value image after the tissue-flickering decision step.

In one embodiment, the tissue-flickering flag reconfirmation step includes performing a statistic region decision on the two-value image, wherein a region is determined surrounding a tissue-flickering flag to be reconfirmed; the number of the tissue-flickering flags in the region is accumulatively counted; and if the number of the tissue-flickering flags is larger than a flag threshold value, the tissue-flickering flag to be reconfirmed remains unchanged; otherwise, the tissue-flickering flag to be reconfirmed is inverted.

In one embodiment, the tissue-flickering flag reconfirmation step includes performing spatial filtering on the two-value image.

In one embodiment, the blood flow image data include the velocity, energy and variance of a blood flow, wherein the first fusing rule includes a first velocity threshold value, a first energy threshold value and/or a first variance threshold value; and the second fusing rule includes a second velocity threshold value, a second energy threshold value and/or a second variance threshold value, wherein the first velocity threshold value and the first energy threshold value are larger than the second velocity threshold value and the second energy threshold value respectively, and the first variance threshold value is smaller than the second variance threshold value.

In one embodiment, in the portion in which tissue flickering exists, when the velocity and the energy of the blood flow are larger than the first velocity threshold value and the first energy threshold value respectively, the blood flow image data are displayed; otherwise, the anatomical image data are displayed; and in the portion in which no tissue flickering exists, when the velocity and the energy of the blood flow are larger than the second velocity threshold value and the second energy threshold value respectively, the blood flow image data are displayed; otherwise, the anatomical image data are displayed.

The present disclosure also provides an ultrasound imaging apparatus for adaptively suppressing tissue flickering, comprising. In one embodiment, the apparatus includes a transmitting and receiving unit for transmitting ultrasound pulses to an object to be detected, and for receiving ultrasound echo signals from the object to be detected. The apparatus also includes an envelope detecting unit for processing the ultrasound echo signals to obtain anatomical image data. The apparatus may further include a signal processing unit for processing the ultrasound echo signals to obtain demodulated signals. In one embodiment, the apparatus also includes a blood flow processing unit for processing the demodulated signals to obtain blood flow image data. The apparatus may further include a displaying unit for displaying either the anatomical image data or the blood flow image data based on fusing rules, wherein the displaying unit uses a first fusing rule for a portion of the object to be detected in which tissue flickering exists, and uses a second fusing rule, which differs from the first fusing rule, for a portion of the object to be detected in which no tissue flickering exists.

In one embodiment, the apparatus further includes a tissue-flickering determination unit for determining the portion of the object to be detected in which tissue flickering exists and the portion in which no tissue flickering exists. The tissue-flickering determination unit may include a filtering device for filtering out stationary tissue components from the demodulated signals to obtain motion components; a parameter estimation device for estimating tissue motion parameters based on the motion components; and a tissue-flickering decision device for deciding the existence of tissue flickering in the object to be detected based on the tissue motion parameters, and for providing a tissue-flickering flag.

In one embodiment, the tissue-flickering determination unit further includes a tissue-flickering flag reconfirmation device for reconfirming the tissue-flickering flag provided by the tissue-flickering decision device.

The four traditional tissue-flickering suppressing solutions directly use tissue echoes for the estimation of tissue motion parameters. However, due to the existence of the stationary tissue components, the estimated tissue motion velocity is on the low side, such that the wall filter can not effectively filter out the tissue motion. The present disclosure has the following advantages compared to the traditional tissue-flickering suppressing solutions.

The disclosure utilizes zero-order linear polynomial regression filtering to filter out stationary tissue components from tissue echoes and retains only motion components, and then estimates tissue motion parameters, thereby making a more precise estimation of the tissue motion velocity.

The disclosure reconfirms the decision of tissue flickering based on the fact that the tissue motion is spatially inter-restricted, making the determination of tissue flickering more reliable.

During the subsequent fusion of anatomical image data and blood flow image data, at a space point in a portion in which tissue flickering exists after reconfirmation, the velocity threshold value and the energy threshold value of the blood flow are accordingly increased, or the variance threshold value of the blood flow is accordingly decreased. That is, the fusion of anatomical image data and blood flow image data is achieved by adjusting the velocity, energy and variance threshold values of the blood flow at different points in space based on tissue-flickering flags, thereby effectively suppressing tissue flickering.

Figure 1:
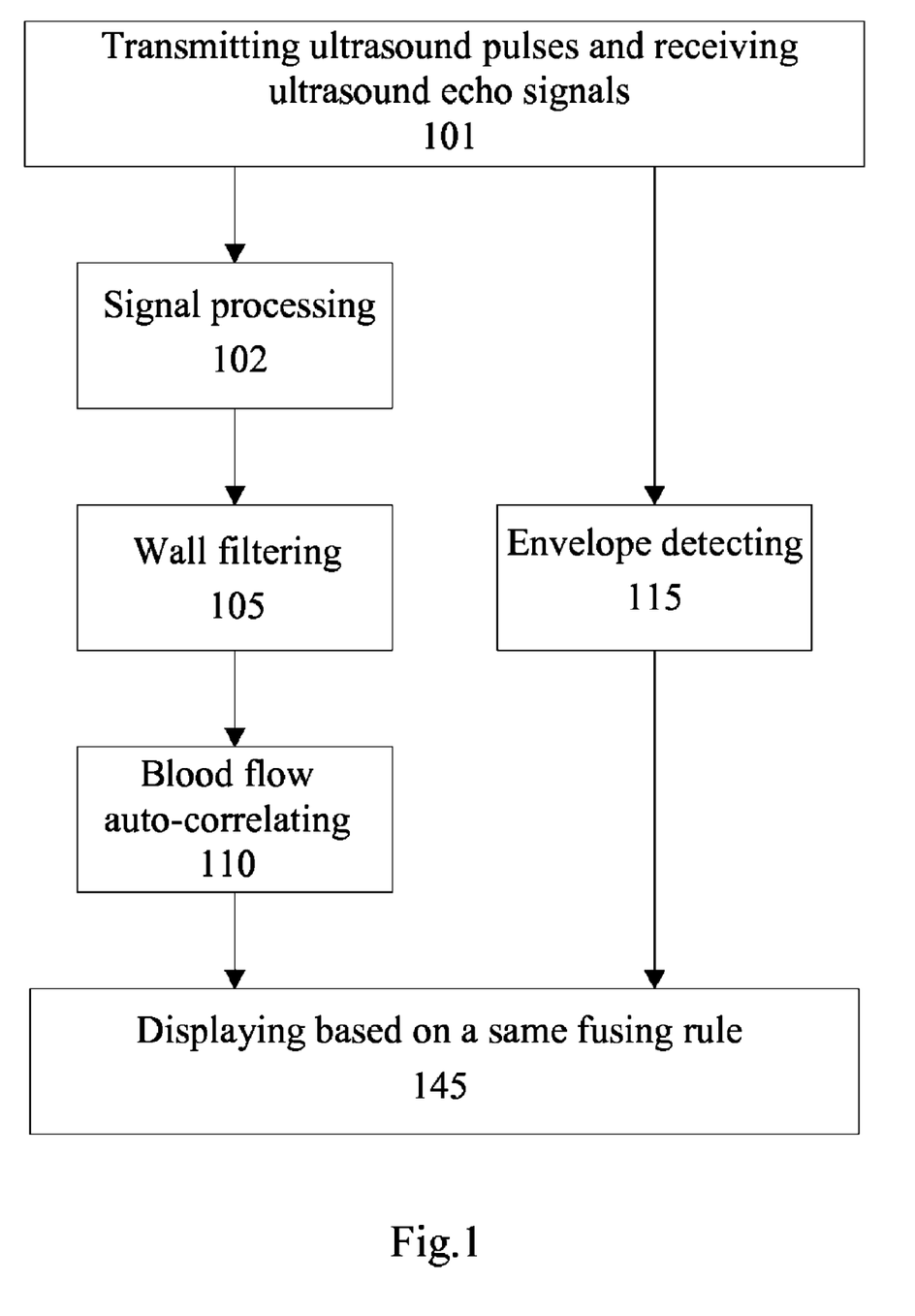
FIG. 1 is a flow diagram of a traditional ultrasound imaging method without adaptive tissue-flickering suppression.

FIG. 1 is a flow diagram of a traditional ultrasound imaging method without adaptive tissue-flickering suppression. In Step 101, ultrasound pulses are transmitted to an object to be detected, and ultrasound echo signals are received from the object to be detected. Typically the ultrasound echo signal is radio frequency signal with frequency of about 2~15 MHz.

In Step 102, the ultrasound echo signals are demodulated to obtain demodulated signals. In one configuration, the radio frequency echo signal is multiplied by $\cos(2\pi f_0 t)$ and $\sin(2\pi f_0 t)$ individually, where $f_0$ is the radio frequency, after which the products are introduced to a low pass filter (LPF). The output of the LPF is a demodulated signal, which is complex signal. The channel multiplying $\cos(2\pi f_0 t)$ gets the real part and the other channel gets the imaginary part. Typically, the frequency of the demodulated signal is less than 100 kHz.

In Step 105, the demodulated signals are wall-filtered. In Step 110, the auto-correlation of the wall-filtered demodulated signals is performed to obtain the velocity, energy and variance of the blood flow. In Step 115, the ultrasound echo signals are processed to obtain anatomical image data. In Step 145, the velocity, energy, variance of the blood flow and the anatomical image data are displayed based on a same fusing rule, thereby providing to a user a two-dimensional image including both the tissue structure and the blood flow dynamics.

Considering particularly tissue flickering caused by heartbeat, respiration, blood vessel wall pulsation in a human body, or the relative motion of a probe, the aforementioned tissue-flickering suppressing solutions in the prior art technologies follow different blood flow processing flows. For solutions such as frequency spectrum shifting, adjustment of wall filter cutoff frequency and characteristic decomposition of correlation matrix, the effectiveness of tissue-flickering suppression depends upon that the Doppler shift of tissue motion moves only towards one direction in a correlation processing period (in a period for 4-16 transmissions). However, the actual situation of the tissue motion is very complicated. It may be a reciprocating motion, a twist, or a tissue motion only in a period of time during correlation processing. In Doppler frequency spectra of tissues caused by the complex tissue motion, some are stationary frequency spectra and some are tissue motion frequency spectra.

If the demodulated signals are directly used for the estimation of tissue motion parameters, the estimated tissue motion velocity will be on the low side. For the solution of the frequency spectrum shifting, since the tissue motion frequency shift for the frequency spectrum shifting is too low such that the shifted frequency spectrum may not be shifted to a direct current, there are still clutter residues after wall-filtering. For the solution of adjustment of wall filter cutoff frequency, since the estimated tissue motion frequency is also too low such that the adjusted wall filter cutoff frequency is not increased or insufficiently increased, there are still strong clutter residues. Such clutter residues accumulate over time, and last for a number of frames. Furthermore, since the calculated tissue-flickering velocity is on the high side due to a problem with the transition band of wall filter magnitude versus frequency response, it is disadvantageous for the suppression of tissue flickering in the subsequent processing.

With regard to the weakness of traditional tissue-flickering suppressing solutions, the disclosed technique improves the detection and estimation of tissue motion parameters, and reconfirms the detected tissue-flickering flags based on the spatial association of tissue motions. For a portion in which tissue flickering exists after reconfirmation, instead of increasing the cutoff frequency of the wall filter, a different fusing rule from that being used for the image fusion of a portion in which no tissue flickering exists is used during the subsequent fusion processing of the black and white tissue image and the blood flow motion parameter image, thereby increasing or decreasing corresponding decision threshold values.

In one embodiment, instead of directly using tissue echoes for auto-correlation, the tissue motion parameters are estimated by filtering out the stationary tissue components from tissue echoes via zero-order linear polynomial regression filtering, and performing the tissue auto-correlation estimation of the remaining motion components. This estimation of tissue motion parameters is not affected by the stationary tissue components and is thus capable of reflecting tissue motion states more precisely. The estimated tissue motion parameters may be used to decide whether a point in the scan space is a case of tissue flickering, and to mark the point with a tissue-flickering flag.

Tissue-flickering flags of all the points in the scan space constitute a tissue-flickering flag image, which is a two-value image. A reconfirmation of tissue-flickering flags is then performed on the two-value image. During the displaying of the anatomical image data and the blood flow image data, the reconfirmed tissue-flickering flags also participate in what is displayed, thereby increasing either or both of the energy threshold value and the velocity threshold value of the color display and/or decreasing the variance threshold value thereof based on the determination of tissue flickering. That is, for the determined portion in which tissue flickering exists, a fusing rule may be used. For the determined portion in which no tissue flickering exists, another fusing rule is used.

Figure 2:
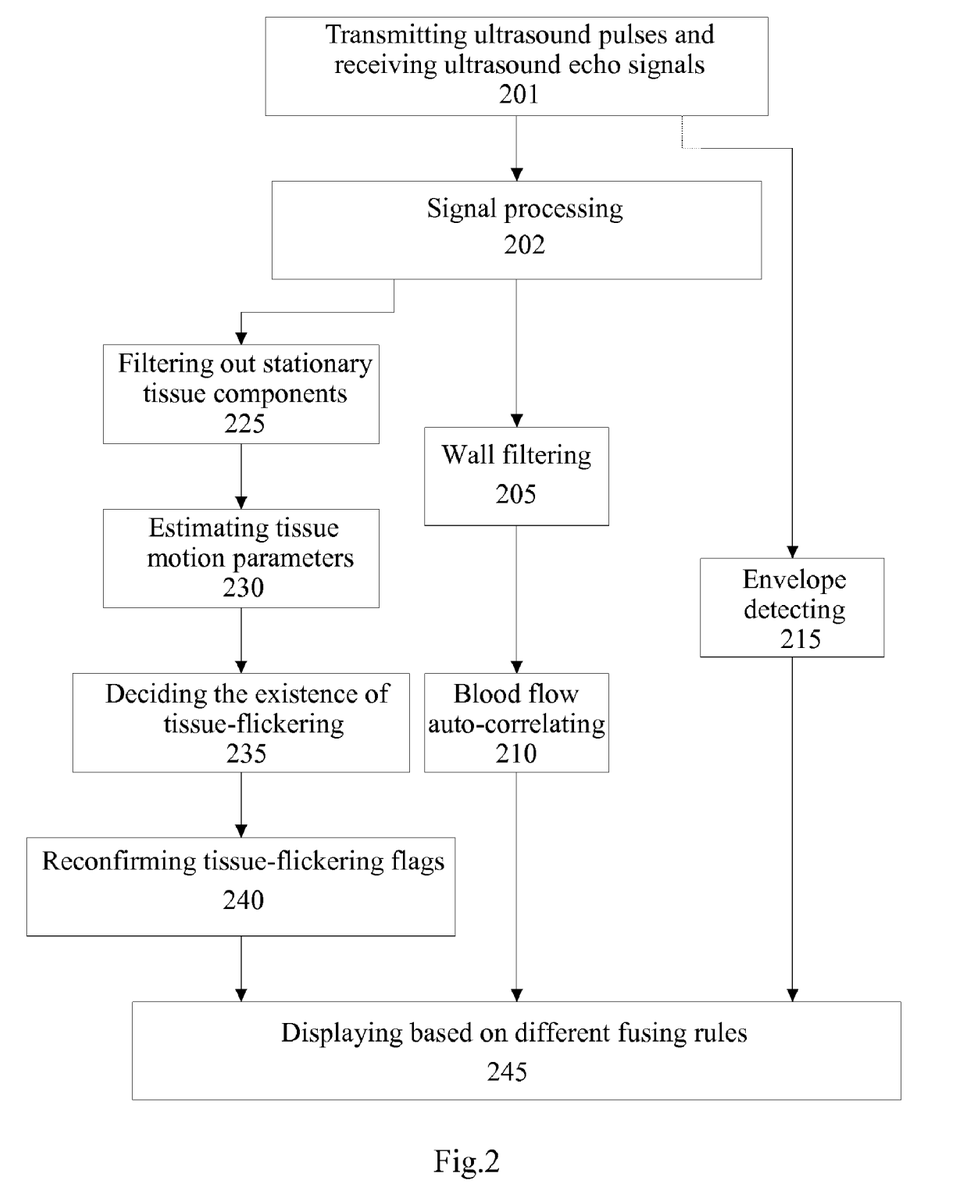
FIG. 2 is a flow diagram of an ultrasound imaging method for adaptively suppressing tissue flickering.

FIG. 2 is a flow diagram of an ultrasound imaging method for adaptively suppressing tissue flickering according to an embodiment of the present disclosure, in which Steps 201, 202, 205, 210, 215 are identical to Steps 101, 102, 101, 102, 105, 110, 115, respectively, and will not be described here in detail.

In Step 225, the stationary tissue components in the demodulated signals are filtered out to obtain the motion components. In one embodiment, this is achieved by zero-order linear polynomial regression filtering of the demodulated signals. In particular, the ultrasound echo signals obtained from the front-end are orthogonally demodulated, low-pass-filtered, and down-sampled, and then sent to a transposition memory. The transposition memory generally stores at least a frame of demodulated signals. After the zero-order linear polynomial regression filtering of the whole frame of demodulated signals, the stationary tissue components are filtered out and the motion components are retained.

It is assumed that in the color mode, the demodulated signal is represented by $x(n)$, $n=1 \ldots N$, with N representing the number of transmissions. The tissue echo $c(n)$ in $x(n)$ may be decomposed into a space in which a group of linear and independent polynomial base vectors are expanded. This group of base vectors is $\{1,n,n^2, \ldots n^K\}$, wherein K represents the number of spatial dimensions.

$$c(n) = \sum_{k=0}^{K-1} a_k n^k$$

In the above equation, $a_k$ is the coefficient of the tissue echo $c(n)$ for the base vector $n^k$, which can be estimated by applying the rule of least mean square error to the reconstructed signal and the original signal. When the base vector is 1, $a_0$ represents the direct current component of the tissue echo, i.e., the stationary tissue component in the tissue echo.

The k-order linear polynomial regression filtering is used to subtract the component in each of (1 to $n^k$)-dimension spaces from the original demodulated signal. The zero-order linear polynomial regression filtering is used to subtract the stationary tissue component from the original demodulated signal, which can be represented by:

$$y(n)=x(n)-a_0$$

The calculation of the zero-order linear regression filtering as shown in the above equation is similar to a conventional wall filtering calculation, which can be realized by a multiplication of the filtering matrix and the demodulated signal.

In one embodiment, the zero-order linear polynomial regression filtering may be replaced with other filtering approaches, such as infinite impulse response filtering, finite impulse response filtering, or the like. Although designs and responses of these filtering approaches are different from each other, stationary tissue components can be filtered out, creating conditions for determining tissue flickering in a more precise manner.

In Step 230, the tissue motion parameters of the demodulated signals from which the stationary tissue components are filtered out are estimated to obtain the tissue motion parameters, including the velocity, energy, and variance of the tissue motion. Since the demodulated signals participating in the estimation of the tissue motion parameters no longer include any stationary tissue components, the tissue motion parameters obtained can more precisely describe the tissue motion characteristics, thus avoiding a rather low estimated tissue motion velocity caused by the existence of the stationary tissue components. In one embodiment, the tissue motion parameters of the demodulated signals whose stationary tissue components are filtered out are estimated by using tissue auto-correlation.

In Step 235, the existence of tissue flickering in the object to be detected is determined based on the estimated tissue motion parameters, and tissue-flickering flags are provided. Generally, for a portion of the scan space wherein the energy, velocity, and variance of the tissue motion are large, tissue flickering may appear. It should be noted that during some examinations of limbs or superficials, there are only stationary tissue echoes in some scan spaces, and after zero-order linear polynomial regression filtering, the stationary tissue echoes are completely filtered out with only noise or blood flow remaining. Since these scan spaces have a large motion velocity and a large motion variance but a relatively small motion energy, differentiation between blood flow or noise and tissue flickering can nevertheless be made.

Figure 3:
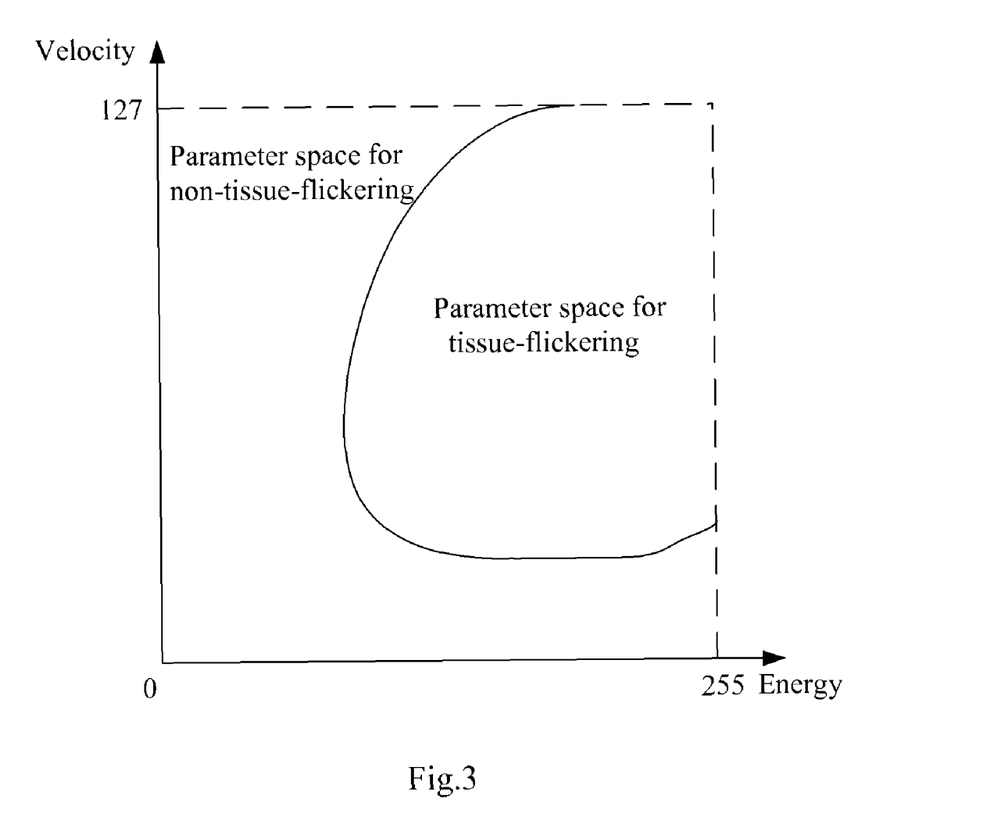
FIG. 3 is a schematic diagram of a parameter distribution for tissue-flickering determination based on the velocity and energy of tissue motion.

In one embodiment, the decision of tissue flickering may be made by means of a lookup table. FIG. 3 is an example of a lookup table using the tissue motion energy and velocity (assuming that both the energy and the velocity are adjusted to 8 bits). The changing curve of a lookup table varies with different examined parts.

In one embodiment, the tissue-flickering flags provided in Step 235 constitute a frame of two-value image, with each tissue tissue-flickering flag is denoted by one bit, wherein 1 represents tissue flickering and 0 represents no tissue flickering (and vice versa). In one embodiment, this two-value image is stored.

It should be noted that the determination of tissue flickering is not limited to the aforementioned application of a lookup table, and may also be processed by using a threshold rule or by other detecting and deciding approaches, such as artificial intelligence, through which a frame of a two-value decision table will finally be generated.

In one embodiment, Step 240 is also included for reconfirming a tissue-flickering flag in the two-value image outputted in Step 235. Since the human body tissue, which differs from the blood flow, is a closely associated tissue structure, and motions at any point and at surrounding points are mutually restrictive, the difference of tissue flickering is spatially small.

In one embodiment, the reconfirmation of tissue-flickering flags is achieved by means of statistic region decision of the two-value image outputted by Step 235. In a two-value image region with the 5×5 spatial aperture surrounding the tissue-flickering flag to be reconfirmed, the number of tissue-flickering flags is accumulatively counted. When the number of tissue-flickering flags is larger than a flag threshold value, the tissue-flickering flag to be reconfirmed remains unchanged; otherwise, the tissue-flickering flag to be reconfirmed is inverted.

Figure 4:
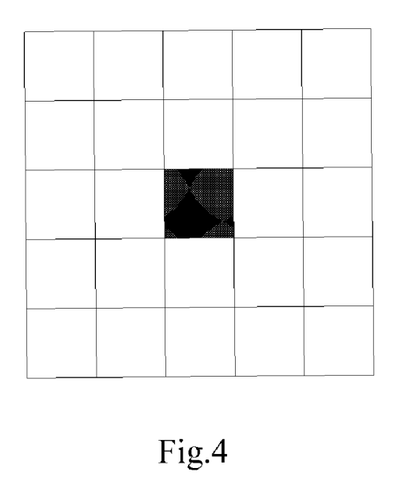
FIG. 4 is a schematic diagram of a spatial aperture during reconfirmation of tissue-flickering flags.

The tissue-flickering flag to be reconfirmed and the surrounding region of 5×5 spatial aperture thereof are shown in FIG. 4. With regard to the reconfirmation of tissue-flickering flags, the spatial region for reconfirmation is not limited to having the spatial aperture as shown in FIG. 4, but may be of any spatial aperture.

In another embodiment, the reconfirmation of tissue-flickering flags is achieved by means of spatial filtering of the two-value image. Alternatively, other two-value image processing methods are used, such that the tissue-flickering flags may finally congregate more rapidly.

It should be noted that in a specific implementation, the reconfirmation of tissue-flickering flags may not be used. In this case, tissue flickering may be similarly reduced at the cost of losing the effectiveness of tissue flickering suppression to some degree.

In Step 245, either anatomical image data or blood flow image data are displayed based on different fusing rules. That is, a first fusing rule is used for the portion of the object to be detected in which tissue flickering exists, and a second fusing rule is used for the portion of the object to be detected in which no tissue flickering exists. The fusing rule to be used may be determined based on the tissue-flickering flags provided in Step 235 or 240. In one embodiment, the fusing rule to be used is determined based on the reconfirmed tissue-flickering flags provided in Step 240.

Figure 5:
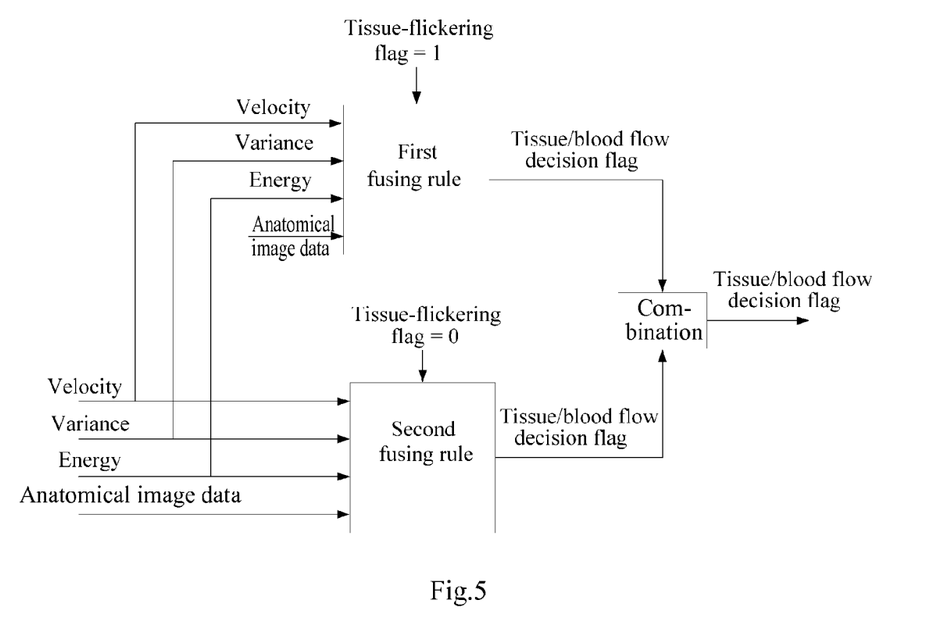
FIG. 5 is a schematic diagram of a display of blood flow image data and anatomical image data based on fusing rules.

FIG. 5 is a schematic diagram of the display of blood flow image data and anatomical image data according to an embodiment of the present disclosure. For a point in the scan space where the reconfirmed tissue-flickering flag is 1, indicating that tissue flickering exists at the point, a first fusing rule is used for the fusion of anatomical image data and blood flow image data; and for a point in the scan space where the reconfirmed tissue-flickering flag is 0, indicating no tissue flickering exists at the point, a second fusing rule is used for the fusion of anatomical image data and blood flow image data. In one embodiment, a tissue/blood flow decision flag is also provided. The tissue/blood flow decision flags outputted based on different fusing rules will be combined to constitute a frame of tissue/blood flow decision flag image spatially, and the image is also a frame of two-value image, with each tissue/blood flow decision flag denoted by one bit.

Figure 6:
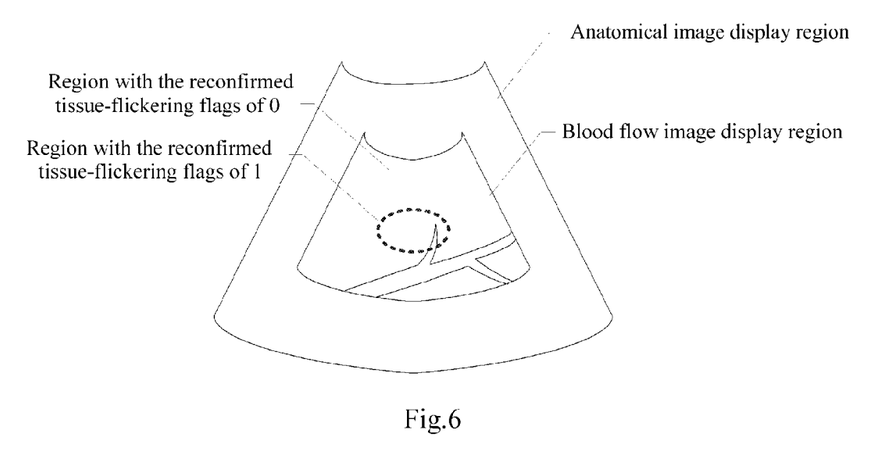
FIG. 6 is a schematic diagram of the detection of tissue flickering.

FIG. 6 is a schematic diagram of the detection of tissue flickering according to one embodiment. As shown in FIG. 6, in the blood flow image display region, the portion surrounded by the dotted line is the portion in which tissue flickering is detected, and the portion outside the dotted line is the portion in which no tissue flickering is detected. For the portion inside the dotted line in which tissue flickering is detected, a first fusing rule is used; and for the portion in which no tissue flickering is detected, a second fusing rule is used.

The simplest fusing rule detects the existence of blood flow based on different threshold values. Generally, if both the velocity and energy of the blood flow are larger than respective thresholds, the blood flow image data are displayed at corresponding spatial points; otherwise, the anatomical image data are displayed at corresponding spatial points. Hereinafter, different fusing rules in the blood flow parameter space (energy, velocity) will be illustrated with reference to FIGS. 7 and 8.

Figure 7:
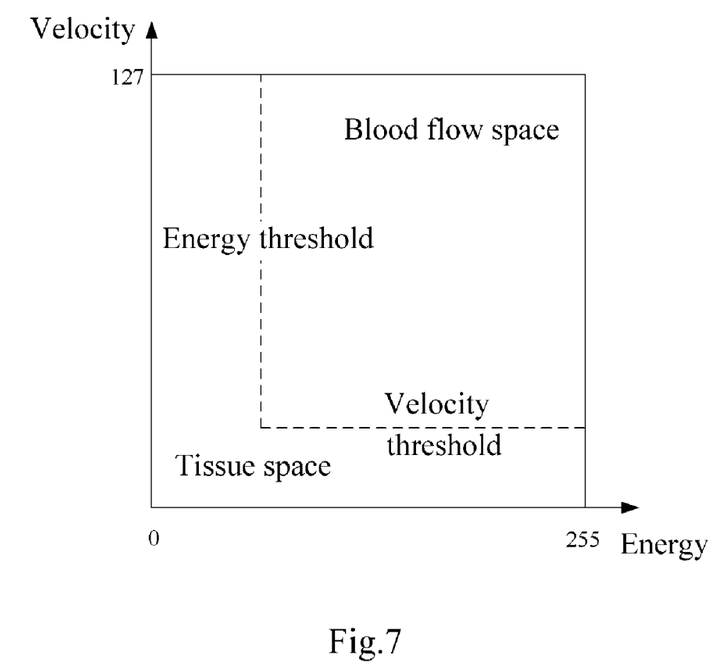
FIG. 7 is a schematic diagram of a fusing rule in a portion in which no tissue flickering exists.

FIG. 7 is a schematic diagram of the fusing rule in the portion in which no tissue flickering exists. As shown in FIG. 7, with respect to the portion of the object to be detected in which no tissue flickering exists, the following conventional fusing rule is used: if the energy of the blood flow at a point in the space is larger than an energy threshold value, and the velocity of the blood flow is larger than a velocity threshold value, the point is determined as blood flow, thereby displaying the blood flow image data; otherwise, the point is determined as tissue, thereby displaying the anatomical image data.

Figure 8:
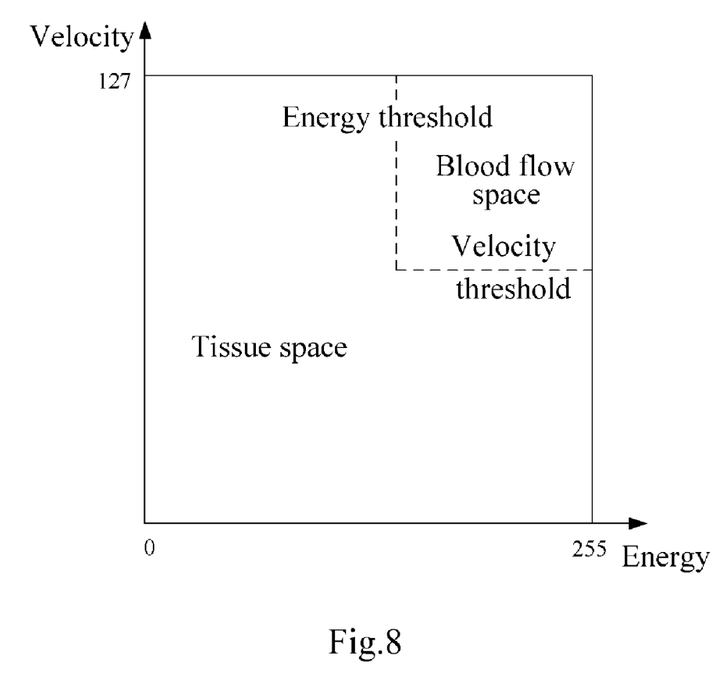
FIG. 8 is a schematic diagram of a fusing rule in a portion in which tissue flickering exists.

FIG. 8 is a schematic diagram of the fusing rule in the portion in which tissue flickering exists. With respect to the portion of the object to be detected in which tissue flickering exists, a special fusing rule is used, in which the threshold values of blood flow energy and velocity are increased. If the blood flow energy of a spatial point in the portion in which tissue flickering exists is larger than the increased energy threshold value, and the blood flow velocity is larger than the increased velocity threshold value, the point is determined as blood flow, thereby displaying the blood flow image data; otherwise, the point is determined as tissue, thereby displaying the anatomical image data.

It should be noted that in the actual displaying step, the fusing rule used also involves anatomical image data and blood flow variances, and the fusing rules applied to different human body parts may be different.

Figure 9:
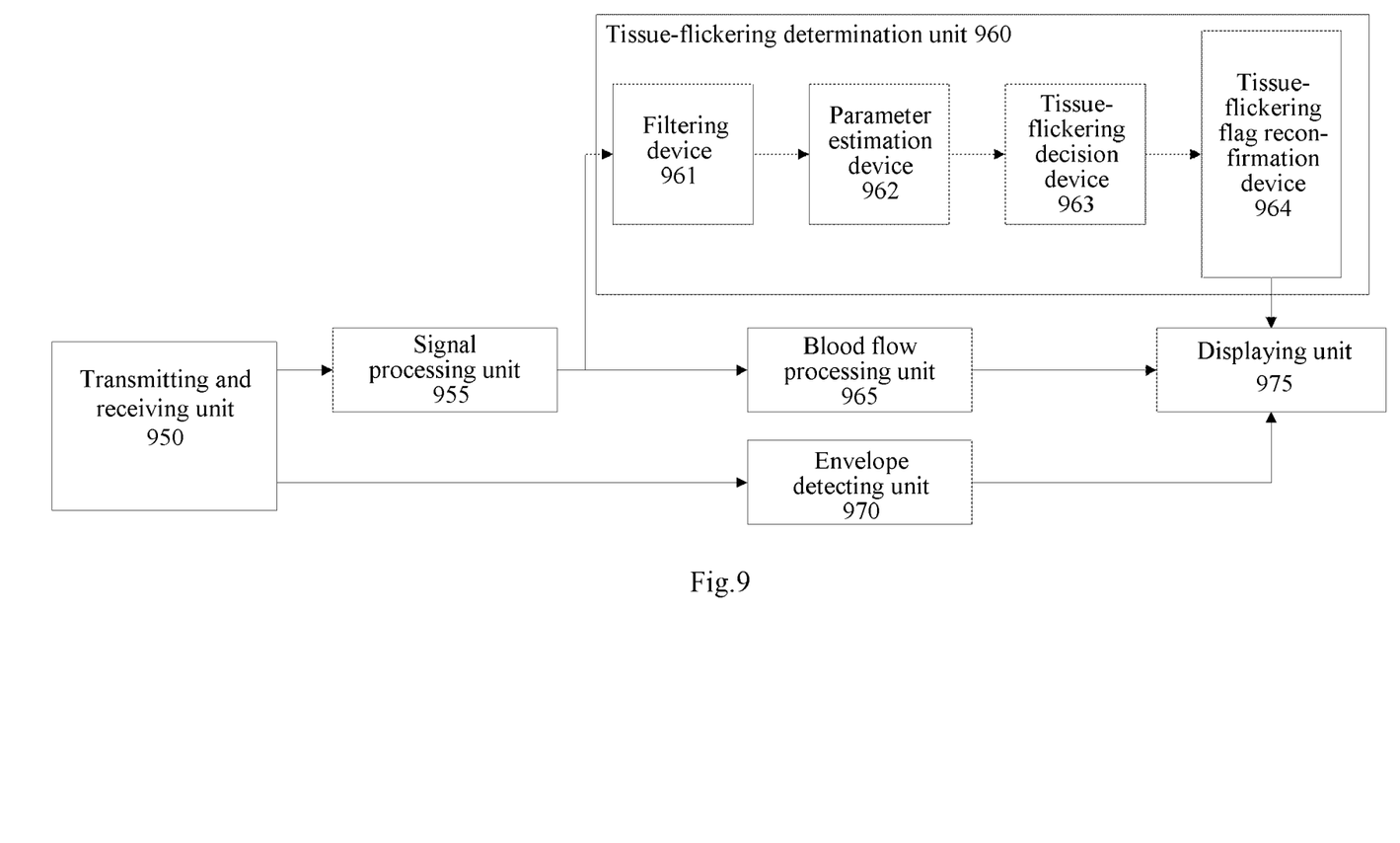
FIG. 9 is a block diagram of an ultrasound imaging apparatus for adaptively suppressing tissue flickering.

FIG. 9 is a block diagram of an ultrasound imaging apparatus for adaptively suppressing tissue flickering according to an embodiment of the present disclosure. As shown in FIG. 9, the ultrasound imaging apparatus may includes a transmitting and receiving unit 950 for transmitting ultrasound pulses to an object to be detected and receiving ultrasound echo signals from the object to be detected; an envelope detecting unit 970 for processing ultrasound echo signals to obtain anatomical image data; a signal processing unit 955 for processing ultrasound echo signals to obtain demodulated signals; a blood flow processing unit 965 for processing the demodulated signals to obtain blood flow image data; and a displaying unit 975 for displaying either the anatomical image data or the blood flow image data based on fusing rules, wherein the displaying unit applies a first fusing rule to a portion of the object to be detected in which tissue flickering exists, and applies a second fusing rule, which is different from the first fusing rule, to a portion of the object to be detected in which no tissue flickering exists.

In one embodiment, the ultrasound imaging apparatus further includes a tissue-flickering determination unit 960 for determining the portion of the object to be detected in which tissue flickering exists and the portion in which no tissue flickering exists. In one embodiment, the tissue-flickering determination unit includes a filtering device 961 for filtering out stationary tissue components from the demodulated signals to obtain motion components; a parameter estimation device 962 for estimating tissue motion parameters based on the motion components; and a tissue-flickering decision device 963 for deciding the existence of tissue flickering in the object to be detected based on the tissue motion parameters, and for providing a tissue-flickering flag.

In one embodiment, the tissue-flickering determination unit 960 further includes a tissue-flickering flag reconfirmation device 964 for reconfirming the tissue-flickering flags provided by the tissue-flickering decision device 963.

Hereinafter is a detailed description of the operation flow of the tissue-flickering determination unit 960 according to an embodiment of the present disclosure. First, the filtering device 961 uses the zero-order linear polynomial regression filtering to filter out stationary tissue components from demodulated signals to obtain motion components. The motion components obtained upon filtering are inputted into the parameter estimation device 962, which performs auto-correlation calculation of the motion components obtained upon filtering to obtain tissue motion parameters. The tissue motion parameters include the velocity, energy, and variance of the tissue motion.

In the tissue-flickering decision device 963, it is determined whether tissue flickering exists at each spatial point of a frame of data based on the tissue motion parameters provided by the parameter estimation device 962 and according to a certain rule, and a frame of a two-value image of tissue-flickering flags is inputted into the tissue-flickering flag reconfirmation device 964. In the two-value image, 1 (or 0) indicates that tissue flickering exists, and 0 (or 1) indicates that no tissue flickering exists. The tissue-flickering flag reconfirmation device 964 accumulatively counts the tissue-flickering flags in a certain region (for example, a 5×5 spatial region as shown in FIG. 5) surrounding a tissue-flickering flag to be reconfirmed.

When the total number of the tissue-flickering flags in this spatial region is larger than the flag threshold value, the tissue-flickering flag to be reconfirmed remains unchanged; otherwise, the tissue-flickering flag to be reconfirmed is inverted. The displaying unit 975 receives the velocity, variance, and energy of the blood flow outputted by the blood flow processing unit 965 and the anatomical image data outputted by the envelope detecting unit 970 and the reconfirmed tissue-flickering flags outputted by the tissue-flickering determination unit 960, and detects the blood flow based on a certain fusing rule. A conventional fusing rule is used for the spatial portion in which no tissue flickering is detected; and a special fusing rule is used for the spatial portion in which tissue flickering is detected. Generally, at the reconfirmed spatial point where tissue flickering exists, it is required to increase the threshold values of the velocity and energy at the spatial point, or decrease the threshold value of the variance at the spatial point.

Although the invention has been described above with reference to the specific embodiments thereof, it is not intended that the invention be limited to the above-mentioned embodiments. Various modifications and alternations may be made to the present invention without departing from the scope of the present invention. The scope of the present invention is defined by the appended claims.

What is claimed is:

1. An ultrasound imaging method for adaptively suppressing tissue flickering, comprising:
   transmitting ultrasound pulses to an object to be detected;
   processing ultrasound echo signals to obtain anatomical image data;
   demodulating the ultrasound echo signals to obtain demodulated signals;
   processing the demodulated signals to obtain blood flow image data;
   determining a portion of the object to be detected in which tissue flickering exists and a portion in which no tissue flickering exists; and
   displaying either the anatomical image data or the blood flow image data based on fusing rules,
   wherein displaying comprises using a first fusing rule for the portion of the object to be detected in which tissue flickering exists, and using a second fusing rule, which differs from the first fusing rule, for the portion of the object to be detected in which no tissue flickering exists.

2. The method according to claim 1, wherein determining comprises:
   filtering out stationary tissue components from the demodulated signals to obtain motion components;
   estimating tissue motion parameters based on the motion components;
   deciding the existence of tissue flickering in the object to be detected based on the tissue motion parameters; and
   providing a tissue-flickering flag.

3. The method according to claim 2, wherein deciding comprises comparing the tissue motion parameters with corresponding parameter threshold values.

4. The method according to claim 2, wherein deciding comprises deciding the existence of tissue flickering in the object to be detected based on a lookup table.

5. The method according to claim 2, wherein deciding comprises using a frame of a two-value image to represent tissue-flickering flag distribution in the object to be detected, wherein each tissue-flickering flag is denoted by one bit.

6. The method according to claim 5, wherein deciding further comprises reconfirming tissue-flickering flags in the two-value image.

7. The method according to claim 6, wherein reconfirming comprises performing a statistic region decision on the two-value image, wherein
   a region is determined surrounding a tissue flickering flag to be reconfirmed;
   the number of the tissue flickering flags in the region is accumulatively counted; and
   if the number of the tissue flickering flags is larger than a flag threshold value, the tissue flickering flag to be reconfirmed remains unchanged; otherwise, the tissue flickering flag to be reconfirmed is inverted.

8. The method according to claim 6, wherein reconfirming comprises performing spatial filtering on the two-value image.

9. The method according to claim 2, wherein filtering comprises one of zero-order linear polynomial regression filtering, infinite impulse response filtering, or finite impulse response filtering.

10. The method according to claim 1, wherein estimating comprises:
    performing auto-correlation estimation on the motion components to obtain the tissue motion parameters.

11. The method according to claim 1, wherein the blood flow image data include the velocity, energy, and variance of a blood flow, wherein
    the first fusing rule includes one or more of a first velocity threshold value, a first energy threshold value, and a first variance threshold value; and the second fusing rule includes one or more of a second velocity threshold value, a second energy threshold value, and a second variance threshold value, wherein the first velocity threshold value and the first energy threshold value are larger than the second velocity threshold value and the second energy threshold value, respectively, and the first variance threshold value is smaller than the second variance threshold value.

12. The method according to claim 11, wherein displaying comprises:

in the portion in which tissue flickering exists, when the velocity and the energy of the blood flow are larger than the first velocity threshold value and the first energy threshold value, respectively, the blood flow image data are displayed; otherwise, the anatomical image data are displayed; and in the portion in which no tissue flickering exists, when the velocity and the energy of the blood flow are larger than the second velocity threshold value and the second energy threshold value, respectively, the blood flow image data are displayed; otherwise, the anatomical image data are displayed.

13. An ultrasound imaging apparatus for adaptively suppressing tissue flickering, comprising:

a transmitting and receiving unit for transmitting ultrasound pulses to an object to be detected, and for receiving ultrasound echo signals from the object to be detected;

an envelope detecting unit for processing the ultrasound echo signals to obtain anatomical image data;

a signal processing unit for processing the ultrasound echo signals to obtain demodulated signals;

a blood flow processing unit for processing the demodulated signals to obtain blood flow image data;

a tissue flickering determination unit for determining the portion of the object to be detected in which tissue flickering exists and the portion in which no tissue flickering exists; and a displaying unit for displaying either the anatomical image data or the blood flow image data based on fusing rules, wherein the displaying unit uses a first fusing rule for a portion of the object to be detected in which tissue flickering exists, and uses a second fusing rule, which differs from the first fusing rule, for a portion of the object to be detected in which no tissue flickering exists.

14. The apparatus according to claim 13, wherein the tissue flickering determination unit comprises:

a filtering device for filtering out stationary tissue components from the demodulated signals to obtain motion components;

a parameter estimation device for estimating tissue motion parameters based on the motion components; and a tissue flickering decision device for deciding the existence of tissue flickering in the object to be detected based on the tissue motion parameters, and for providing a tissue flickering flag.

15. The apparatus according to claim 14, wherein the tissue flickering determination unit further comprises a tissue flickering flag reconfirmation device for reconfirming the tissue flickering flag provided by the tissue flickering decision device.

16. An ultrasound imaging apparatus for adaptively suppressing tissue flickering, comprising:

means for transmitting ultrasound pulses to an object to be detected;

means for receiving ultrasound echo signals from the object;

means for processing the ultrasound echo signals to obtain anatomical image data;

means for demodulating the ultrasound echo signals to obtain demodulated signals;

means for processing the demodulated signals to obtain blood flow image data;

means for determining the portion of the object to be detected in which tissue flickering exists and the portion in which no tissue flickering exists; and means for displaying either the anatomical image data or the blood flow image data based on fusing rules, wherein displaying comprises using a first fusing rule for a portion of the object to be detected in which tissue flickering exists, and using a second fusing rule, which differs from the first fusing rule, for a portion of the object to be detected in which no tissue flickering exists.

17. An ultrasound imaging method for adaptively suppressing tissue flickering, comprising:

transmitting ultrasound pulses to an object to be detected;

processing ultrasound echo signals received from the object to obtain anatomical image data and blood flow image data;

determining a portion of the object to be detected in which tissue flickering exists and a portion in which no tissue flickering exists; and displaying either the anatomical image data or the blood flow image data based on fusing rules, wherein displaying comprises using a first fusing rule for the portion of the object to be detected in which tissue flickering exists, and using a second fusing rule, which differs from the first fusing rule, for the portion of the object to be detected in which no tissue flickering exists.

* * * * *